United States Patent [19]

Illum

[11] Patent Number: 5,744,166
[45] Date of Patent: *Apr. 28, 1998

US005744166A

[54] DRUG DELIVERY COMPOSITIONS

[75] Inventor: Lisbeth Illum, Nottingham, United Kingdom

[73] Assignee: Danbiosyst UK Limited, Nottingham, United Kingdom

[*] Notice: The term of this patent shall not extend beyond the expiration date of Pat. No. 5,554,388.

[21] Appl. No.: 576,877

[22] Filed: Dec. 21, 1995

Related U.S. Application Data

[63] Continuation-in-part of Ser. No. 167,611, Dec. 14, 1993, Pat. No. 5,554,388, which is a continuation of Ser. No. 743,328, Aug. 20, 1991, abandoned.

[30] Foreign Application Priority Data

Feb. 25, 1989 [GB] United Kingdom ............ 89045370

[51] Int. Cl.$^6$ .................. A61K 9/50; A61K 9/14; A61K 9/20; A61K 47/36
[52] U.S. Cl. .................. 424/501; 424/426; 424/428; 424/430; 424/434; 424/435; 424/436; 424/437; 424/464; 424/469; 424/499; 514/772.3; 514/777; 514/778
[58] Field of Search .................. 424/426, 428, 424/430, 434, 435, 436, 437, 464, 469, 499; 514/772.3, 777, 778; 530/303

[56] References Cited

U.S. PATENT DOCUMENTS 4,946,870  8/1990  Partain, III et al. ............ 514/777

*Primary Examiner*—Carlos Azpuru
*Attorney, Agent, or Firm*—Arnall Golden & Gregory, LLP

[57] ABSTRACT

Compositions for delivery of pharmacologically active agents and methods for their administration are provided. In one embodiment, the compositions include a complex of a polycationic polymer and a pharmacologically active agent in a pharmaceutically acceptable carrier. The compositions in one embodiment permit transport of pharmacologically active compounds across mucosal membranes for systemic delivery. The polycationic polymer may be, for example, a polycationic carbohydrate such as a chitosan or a chitosan salt or derivative. The therapeutic agent a preferred embodiment is a vaccine or a nucleic acid, such as a gene or antisense oligonucleotide. The composition may be provided in different forms such as a solution, dispersion, powder or in the form of microspheres.

41 Claims, No Drawings

DRUG DELIVERY COMPOSITIONS

This application is a continuation-in-part of U.S. application Ser. No. 08/167,611, filed Dec. 14, 1993, now U.S. Pat. No. 5,554,388, which is a continuation of U.S.Ser. No. 07/743,328, filed Aug. 20, 1991, now abandoned, which corresponds to PCT/GB90/00291, filed Feb. 23, 1990, which claims priority to GB patent application 89 04370.7, filed Feb. 25, 1989, the disclosures of which are incorporated herein by reference.

The present invention relates to drug delivery compositions including therapeutically active drugs and a polycationic polymer which permit improved delivery of the therapeutically active compounds to a patient.

BACKGROUND

The effective delivery of pharmaceutical compositions can be difficult. A major problem in drug delivery is the effective transfer of high molecular weight material such as proteins and peptides across biological membranes. Normally such molecules are not taken up by the body systemically if administered to the gastrointestinal tract, the buccal mucosa, the rectal mucosa, the vaginal mucosa or the nasal mucosa.

Recent studies with insulin have demonstrated that the absorption of high molecular weight compounds across biological membranes can be increased if administered in conjunction with compounds termed "absorption enhancers" or "absorption promoters". These absorption enhancing materials include surfactants of the non-ionic type as well as various bile salts and bile salt derivatives, such as fusidic acid. The literature in the field of gastroenterology contains a wide range of surfactant materials used as absorption promoters to increase the permeability of biological membranes. (For a review see Davis et al. (Editors), *Delivery Systems for Peptide Drugs*, Plenum Press, New York, 1987.) However, such materials are known to have irritant effects on membranes, and therefore, may not be suitable for the chronic administration of pharmacological agents.

EP-A-023 359 and EP-A-122 023 describe a powdery pharmaceutical composition for application to the nasal mucosa and methods for administration thereof, which permits polypeptides to be absorbed through the nasal mucosa. U.S. Pat. No. 4,226,848 describes a method for administering a powdery medicament to the nasal mucosa where the preferred composition has mucoadhesive properties. Mucoadhesives are disadvantageous in that they are primarily a retention system rather than a transport facilitator.

EP-A-230 264 describes an aqueous nasal drug delivery system for vaccines containing a high molecular weight drug, a gelling agent, such as hydroxyethylcellulose, and in some cases other additives, such as surfactants, glycerol and polyethyleneglycol, which are administered as a powder.

Microsphere-containing formulations have been described in WO 88/09163. The formulations contain certain enhancers to aid transport of a drug across the mucosa. WO 89/03207 describes formulations which do not require an enhancer, which include drug-containing microcapsules that are coated with DEAE-dextran.

DEAE-dextran has been proposed for use in oral drug delivery formulations, where it is believed to interact with gastrointestinal mucins. Anderson, M. T. et al., oral presentation at a meeting of the Society for Experimental Biology, 24–29 Jul. 1988, Manchester, U.K. DEAE-dextran has been delivered to the nasal cavities of rabbits as a model compound to study the absorption of peptides of differing sizes. Maitani, Y., et al., *Int. J. Pharm.*, 49:23–27(1989).

Igawa et al., *Chem. Pharm. Bull.*, 36(8):3055–3059 (1988), disclose the intranasal administration of human interferon-β with a DEAE-dextran excipient to rabbits. The dextran had an average molecular weight (MW) of 9000 and did not enhance the absorption of the drug. The authors concluded that low MW excipients were to be preferred to high MW components.

GB-A-2 092 002 discloses magnesium and calcium-chelating compounds for enhancing the absorption of drugs, such as polyamino acids, through a digestive organ. Sawanagi et al., *Chem. Pharm. Bull.*, 30(11):4216–4218 (1982), discloses the use of chitosan to bind the ingredients of tablets for retention in the mouth. Delivery to non-oral mucosal surfaces was not disclosed.

U.S. Pat. No. 4,946,870 to Partain, III. et al. discloses a delivery system including pharmaceutical agents and an aminopolysaccharide, such as chitosan and chitosan derivatives, which forms a film when topically applied. Chitosan has previously been used to precipitate proteinaceous material, to make surgical sutures and as an immunostimulant. It has also been employed in oral drug formulations in order to improve the dissolution of poorly soluble drugs (Sawayanagi et al., *Chem. Pharm. Bull.*, 31:2062–2068 (1983)) or for the sustained release of drugs (Nagai et al., *Proc. Jt. US-Jpn. Semin. Adv. Chitin, Chitosan, Relat. Enzymes*, Zikakis J. P. (Ed), Academic Press, Orlando, pages 21–39, 1984) by a process of slow erosion from a hydrated compressed matrix.

It is therefore an object of the invention to provide compositions for delivery of pharmacologically active agents to a patient in therapeutically effective amounts. It is a further object to provide compositions which permit the transport of pharmacologically active agents across mucosal surfaces and the systemic distribution of the pharmaceutical agents in the patient. It is a further object to provide compositions that enhance the absorption of such agents by mucosal membranes but does not confine the distribution to the region of application. It is a further object of the invention to provide compositions which permit the delivery of pharmacologically active agents such as organic compounds, vaccines and genes to a patient.

SUMMARY

Pharmaceutical compositions and methods for their use are provided, wherein the compositions include a pharmacologically active agent and a polycationic polymer in a pharmaceutically acceptable carrier. The composition can be provided in a form, such as a powder or solution, which is suitable for the route of administration to be used. For example, the composition may be provided in a form which is administered to mucosa of a mammal where it remains at the site of administration for a sufficient time to permit systemic delivery of the pharmacologically active agent. The composition may include a covalent or ionic complex of the polycationic polymer, such as a chitosan compound, and the pharmacologically active agent. The pharmacologically active agent in one embodiment can be a nucleic acid, such as a gene, an antisense nucleotide, or a ribonucleic acid. The compositions may be administered, e.g., orally, topically or by inhalation, i.e., to the lung or the nose, to permit delivery of the pharmacologically active agent in a therapeutically effective amount to a patient.

DETAILED DESCRIPTION

Compositions including a polycationic polymer and a pharmacologically active agent are provided for administration to a mammal. The polycationic polymer, as defined herein, includes a plurality of cationic groups. In one embodiment, the polycationic polymer is characterized in that (i) the polycationic polymer is not a polyamino acid which chelates calcium or magnesium ions, (ii) the composition does not consist of microcapsules coated with DEAE-dextran, (iii) the composition does not consist of the active compound and a solution of DEAE-dextran when administered to the gut mucosa, and/or (iv), the composition does not comprise chitosan when in the form of a tablet for retention in the mouth. The compositions advantageously permit the pharmaceutically active agent to be administered in therapeutically effective amounts.

POLYCATIONIC POLYMERS

The pharmaceutical compositions can include any of a wide range of polycationic polymers which promote delivery of a therapeutically effective amount of the pharmacologically active agent to a mammal upon administration.

In one embodiment, compositions can be formulated for delivery of the pharmacologically active agent across mucosal membranes. For example, a solution of relatively high molecular weight DEAE-dextran or other polycationic polymer, such as chitosan, can be provided in a formulation which does not require other absorption enhancers, although other enhancers may be included. Diethylaminoethyl-dextran (DEAE-dextran) is a polycationic derivative of dextran containing diethylaminoethyl groups coupled to the glucose residues by ether linkages. The parent dextran can have an average molecular weight of about 5,000 to $40 \times 10^6$, but is typically about 500,000. As used herein, the term includes generally dextrans of MW 10,000 or more. The nitrogen content is usually approximately 3.2% which corresponds to one charged group to three glucose units. "Tandem" groups, which are introduced as the result of side reactions, result in the presence of three different basic groups in approximately equal ratios.

Chitosan is deacetylated chitin, or poly-N-acetyl-D-glucosamine. It is available from Protan Laboratories Inc, Redmond, Wash. 98052, USA and, depending on the grade selected, can be soluble in water up to pH 6.0. A 1% solution of non-water soluble chitosan (Sea Cure) may be made by making a slurry (e.g., 2 g/100 ml) in water and adding an equal volume of organic acid (e.g., 100 ml of 2% acetic acid) and stirring vigorously for one hour. Water-soluble chitosan (Sea Cure$^+$) may dissolve without organic or inorganic acids being present.

DEAE-dextran and chitosan compounds are preferred, but other polycationic polymers including polycationic carbohydrates can be used. As used herein, the term "chitosan compounds" includes chitosan, inorganic or organic salts of chitosan, and any chemically modified forms of chitosan or chitosan derivatives, preferably more positively charged forms.

Other useful polycationic polymers include poly (aminoacids) such as polylysine; polyquaternary compounds; protamine; polyimines; polyvinylamines; polycationic polymers derivatized with DEAE, such as complexes of DEAE with methacrylate, acrylamide, polyimines, albumin, pullulans, celluloses or starches (referred to herein as "DEAE compounds"); polyvinylpyridine; polymethacrylates; polyacrylates; polyoxethanes; polythiodiethylaminomethylethylene (P(TDAE)); polyhistidine; polyornithine; poly-p-aminostyrene; polyoxethanes; co-polymethacrylates (e.g., copolymers of HPMA; N-(2-hydroxypropyl)-methacrylamide); GAFQUAT (disclosed in U.S. Pat. No. 3,910,862, polyvinylpyrrolidonedimethylaminomethylmethacrylates and polyvinylpyrrolidonemethylacrylaminopropyltrimethyl ammonium chlorides); and polyamidoamines. Polycationic polymers that can be used also include cationised gelatins; cationised albumin; "acid" gelatin derived from acid cured tissue; polyethylene glycol (PEG) derivatives of polycationic polymers; cationic phospholipids; and cationic starches.

The polycationic polymers preferably have a molecular weight of 10,000 or more, preferably at least 100,000 or 200,000 and most preferably at least about 500,000. The chitosan (or a salt thereof) preferably has an intrinsic viscosity of at least 400 ml/g, more preferably at least 500, 750 or 1000 ml/g in water.

Optionally, other enhancers may be included in the compositions, such as lysophosphatidylcholine and those disclosed in WO 88/09163, the disclosure of which is incorporated by reference. Gelling agents or viscosity-increasing substances, such as hydroxy-propyl-methylcellulose (HPMC), gelatine, or Poloxamer 407™ may be added in order to help retain the formulation on the mucosa. The chitosan, in particular, may be formulated as microspheres with or without albumin.

THERAPEUTIC AND DIAGNOSTIC AGENTS

The compositions may include any of a wide range of pharmacologically active agents available in the art. The term "pharmacologically active agent" includes any substance having a pharmacological effect including, for example, therapeutic drugs, vaccines and components thereof (such as isolated antigens or fragments), monoclonal antibodies and other compounds capable of having a therapeutic effect when administered to mucosal surface.

Exemplary pharmacologically active compounds include: insulin, calcitonins (for example, porcine, human, salmon, chicken or eel) and synthetic modifications thereof, enkephalins, luteinizing hormone releasing hormone (LHRH) and analogues (such as Nafarelin, Buserelin, and Zoladex), growth hormone releasing hormone (GHRH), nifedipin, thymic humoral factor (THF), calcitonin gene related peptide (CGRP), atrial natriuretic peptide, antibiotics, metoclopramide, ergotamine, Pizotizin, nasal vaccines, (such as AIDS vaccines, influenza, pertussis, measles, rhinovirus Type 13 and respiratory syncitial virus), pentamidine and cholecystykinin (CCK).

Other exemplary compounds include: antibiotics and antimicrobial agents, such as tetracycline hydrochloride, leucomycin, penicillin, penicillin derivatives, erythromycin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitro-glycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, and active vitamin $D_3$; sex hormones; hypotensives; sedatives; anti-tumor agents; steroidal anti-inflammatory agents such as hydro-cortisone, prednisone, fluticasone, prednisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, mefanamic acid, ibuprofen, diclofenac sodium, indomethacin, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents and antitussive-expectorant antiasthmatic agents such as sodium chromoglycate, codeine phosphate, and isoproterenol hydrochloride; analgesics; and anti-migraine compounds.

Other pharmacologically active agents which can be used include nucleic acids, including ribonucleic acids and deoxyribonucleic acids. For example, the compositions may include pharmacologically active antisense nucleotides, ribozymes, external guide sequences for RNAse P, or genes. The incorporation of the nucleic acid into the polycationic polymer improves the delivery of the nucleic acid to the site where it is needed. For example, the composition may be administered to and transported across mucosal surfaces for systemic delivery. The nucleic acid can be complexed with the polycationic polymer, such as a chitosan compound, for example, by a covalent or ionic linkage.

Diagnostic agents which can be used include imaging agents such as air, or other gases such as argon, or nitrogen. Imaging agents which may be utilized include commercially available agents used in positron emission tomography (PET), computer assisted tomography (CAT), single photon emission computerized tomography, x-ray, fluoroscopy, and magnetic resonance imaging (MRI). Microparticles loaded with these agents can be detected using standard techniques available in the art and commercially available equipment.

Examples of suitable materials for use as contrast agents in MRI include the gatalinium chelates currently available, such as diethylene triamine pentacetic acid (DTPA) and gatopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte. Other useful materials include barium for oral use and non-soluble salts such as ZnAc.

METHODS OF PREPARATION

Compositions including the pharmacologically active or diagnostic agent and the polycationic polymer can be prepared as a solution, dispersion, powder or microsphere or other form suitable for a particular application. The pharmacologically active or diagnostic agent and the polycationic polymer optionally can be provided in the form of an ionic or covalent complex formed using methods available in the art.

The compositions may be prepared by dispersing or dissolving the polycationic polymer and the agent in an aqueous solution at a neutral pH, e.g., pH 6.5 to 7.5, preferably about 7.3, using, for example, a standard phosphate buffer, or at a lower pH, for example pH 4, by addition of HCl to the above or by use of an alternative buffer system. DEAE-dextran or chitosan in combination with at least some drugs, such as insulin and other proteins, form a complex. At lower or higher pHs, away from the isoelectric point of the polycation and the drug, this complex may be present as a true solution instead of a dispersion. This may be advantageous, although very low pHs are more likely to irritate or even harm the mucosa. Thus, minor adjustments may need to be made by the routine methods described above to reach the optimal pH. The pH of the solution used to prepare the solution or the complex can be between 1.0 and 11.0, preferably between about 4.0 and 7.5, for example, between about 4.0 and 6.0. Using this procedure, the complex forms in the solution and optionally can then be isolated in solid form, as a powder or microsphere using methods available in the art.

The polycationic polymer may be prepared as a solution in an aqueous medium, a dispersion in an aqueous system, a powder or microspheres. Preferably, the microspheres are formed from the polycationic substance itself (usually with the pharmacologically active substance incorporated therein) with or without other suitable microsphere-forming substances such as (human) serum albumin and derivatives and analogues thereof available in the art. Preferably, the concentration of the polycationic polymer in aqueous solution is about 0.01 to 50% weight/volume ("w/v"), more preferably about 0.1 to 50%, more preferably 0.2% to 30%, and most preferably 0.25 to 15%.

FORMULATIONS

The compositions may be provided in the form of, for example, solid dosage forms including tablets, pellets, mini-tablets, hard gelatin capsules or coated semi-solid preparations, such as soft gelatin capsules. The compositions also may be provided as powders, microspheres, solutions and dispersions and other forms known in the art. Formulations suitable for delivery of drugs to specific mucosal surfaces, such as nasal buccal or other surfaces, can be prepared using methods known in the art of pharmaceuticals.

For example, formulations for delivery to the gastrointestinal system, including the colon, include enteric coated systems, based, e.g., on methacrylate copolymers such as Eudragit L™ (Poly(methacrylic acid, methyl methacrylate)), are only soluble at pH 6 and above, so that the polymer only begins to dissolve on entry into the small intestine. The site where the formulation disintegrates then is dependent on the rate of intestinal transit and the amount of polymer present. A relatively thick polymer coating is used for delivery to the proximal colon. Hardy et al., *Aliment. Pharmacol. Therap.*, 1:273–280 (1987). Polymers capable of providing site-specific colonic delivery can be used which typically rely on the bacterial flora of the large bowel to provide enzymatic degradation of the polymer coat and hence release of the drug. For example, azopolymers (Saffran et al., U.S. Pat. No. 4,663,308), glycosides (Friend et al., *J. Med. Chem.*, 27:261–266 (1984)) and a variety of naturally available and modified polysaccharides (PCT GB 89/00581) can be used.

Pulsed release technology (U.S. Pat. No. 4,777,049 to Magruder et al.) which permits drug delivery at a predetermined time can be used. Such systems can be used to deliver both the therapeutic or diagnostic agent and the polycationic substance, optionally together with other additives that may alter the local microenvironment to promote drug stability and uptake, directly to the colon, without relying on external conditions to provide in vivo release, except for the presence of water.

ADMINISTRATION

The compositions can be administered as required. The compositions may be formulated using pharmaceutically acceptable carriers available in the art for the particular mode of administration used. The pharmacologically active agent is provided in the composition at a concentration which permits delivery in a therapeutically effective amount. The concentration of the active agent is adjusted as needed, for example, to provide therapeutically effective amounts for systemic delivery.

For example, the composition may be administered to mucosal membranes orally, by topical administration or by inhalation through the nasal and pulmonary routes. The compositions can be administered to mucosal membranes, including those of the gastrointestinal tract, the buccal mucosa, the rectal mucosa and the vaginal mucosa. The compositions may be formulated for administration to mucosal surfaces of humans or animals including mucosal surfaces of the vagina, eye, colon or nasal cavity.

The compositions can be administered nasally using a spray device, pressurized aerosol canister, or simple instillation means, or other means known in the art. The compositions may gel on the mucosa, at least to some extent, and this may facilitate retention of the composition on the mucosa, however, this retention function is only supplemental to the primary function of facilitating transport across the membrane for systemic distribution of the pharmacologically active agent.

The present invention will be further understood from the following non-limiting examples.

EXAMPLE 1

Insulin and DEAE-Dextran

A rat in vivo experimental model, modified from that originally described by Hirai et al., *Int. J. Pharm.*, 7:317–325 (1981), and Fisher et al., *J. Pharm. Pharmacol.*, 39:357–362 (1987), was used to study the intranasal absorption of insulin aqueous solutions. Male Wistar rats (Bantin and Kingman) of approximate weight 200–250 g, fasted overnight for about 20 hours, are anesthetized by i.p. injection of 80 mg/kg pentobarbitone sodium (60 mg/ml Sagatal™, May and Baker) with further i.p. injections of 0.05 ml when necessary to maintain a suitable level of anaesthesia. The rats are tracheotomized, the esophagus sealed and the carotid artery and jugular vein cannulated.

Insulin (semisynthetic human Na-insulin) solutions were prepared in 1/75 M phosphate buffer of pH 7.3 to give a concentration of 167 IU/ml and the DEAE-dextran added to give concentrations of 10% w/v, 5% w/v or 1% w/v. The DEAE-dextran used in these experiments has a molecular weight of 500,000.

It is also possible to make up a solution of 334 IU/ml of insulin in phosphate buffer and add equal volumes of the DEAE-dextran in phosphate buffer of 20, 10 or 2% strength. This will give the same end solutions. When mixing the insulin solution with the DEAE-dextran the solution becomes turbid indicating that an interaction between the insulin and the DEAE-dextran has taken place. An insulin solution containing the Laureth-9 enhancer system was prepared in a similar way.

The insulin solution alone or the insulin solutions containing the Laureth-9 or the various concentrations of DEAE-dextran were administered nasally to rats (n=4) at 16.7 IU/kg body weight using a Hamilton microsyringe. A volume of 20 μl was administered.

Blood samples of 0.2 ml were collected in Fluoride oxalate tubes from the carotid artery at 10 and 5 min. prior to the insulin administration and at 5, 15, 30, 45, 60, 90, 120, 180, 240 and 300 min. post-administration. The samples were kept for a short time on crushed ice until analyzed on a Yellow Springs 23 AM glucose analyser by the glucose oxidase method.

Table 1 shows the approximate glucose levels (mmol/l) of rats given a dose of insulin in phosphate buffer and doses of insulin in phosphate buffer (pH 7.3) containing 1%, 5% or 10% DEAE-dextran measured at 120 minutes after administration. The level at the time of administration was about 3.5 to 4.0 mmol/l. The results show that insulin given intranasally as a simple phosphate buffer solution (pH 7.3) does not significantly lower the blood glucose level, whereas the addition of the DEAE-dextran causes fast and significant decreases in blood glucose levels. The effect increases with increasing concentration of DEAE-dextran. The rats given the 10% concentration died early of hypoglycemia. Administration of phosphate buffer alone shows a similar trend to that of the insulin solution alone, i.e., an increase in plasma glucose from about 3.5 to 4.0 mmol/l to about 5 mmol/l.

TABLE 1

Blood Glucose Levels

|  | (mmol/l) |
|---|---|
| Insulin + DEAE-dextran 1% | 1.6 |
| Insulin + DEAE-dextran 5% | 1.2 |
| Insulin + DEAE-dextran 10% | 1.0 |
| Insulin alone | 5.1 |
| Control | 5.0 |

For comparison, the glucose levels of rats given a dose of insulin in phosphate buffer and rats given a dose of insulin in phosphate buffer containing 0.5% Laureth-9 show that this well known effective enhancer system gives a decrease in blood glucose concentration similar to the 1% DEAE-dextran (about 1.9 mmol/l at 120 mins).

EXAMPLE 2

Effect of pH on Insulin/DEAE-Dextran Solutions

Solutions containing DEAE-Dextran 1% w/v and Na-Insulin 167 IU/ml were prepared, separately and combined, in phosphate buffer (pH 7.3) and their pH measured using a Gallenkamp pH stick. The appearance of each solution was noted. The effect of addition of 1M sodium hydroxide solution (NaOH) or 0.1M hydrochloric acid (HCl) was determined. The two separate solutions were each clear (DEAE-D pH 6.58; Insulin pH 7.38) whereas the mixture (pH 6.65) was turbid.

The addition of 0.1M HCl to solutions of DEAE-dextran alone had no effect on solution appearance which remained clear. Solutions of Na-insulin however, became turbid when the pH reached 6.65 but cleared after further addition of acid lowered the pH to 4.14. Solutions of DEAE-dextran combined with Na-Insulin became less turbid after the addition of acid and were clear at pH 4.14. The addition of 1.0M NaOH to solutions of DEAE-dextran and Na-insulin alone had no effect on solution appearance which remained clear. Combined solutions of DEAE-dextran and Na-insulin however became less turbid as the pH increased and formed a clear solution when the pH reached 9.32. Solutions of DEAE-dextran and Na-insulin at about pH 4.0 were found to be at least as effective as those at about pH 6.6 in the rat model described above.

EXAMPLE 3

Toxicity Studies

The effects of a insulin 100 IU/ml and DEAE-Dextran 5% w/v formulation on the nasal mucosa in rats (after 60 min incubation) were less dramatic than those of prior art surfactant enhancers. A few cells lost from the septum and turbinates were visible and mucus discharge on the dosed side resulted in a slight decrease in epithelium height. The clear cell structure was not so well defined and cytoplasmic space appeared reduced. The epithelium still appeared to be more than one cell thick (i.e. pseudostratified) and formed a continuous layer, though the arrangement of nuclei above the basement membrane was altered. Cilia were not always distinct amongst the discharged mucus.

Considerable amounts of AB staining mucus were still apparent in cells on the dosed side, though there was generally not the confluent spread of filled goblet cells as on the undosed side. Some mucus was again present in the undosed cavity of some animals. Effects of this formulation were generally restricted to the ventral half of the cavity and lateral nasoturbinate, i.e., the dorsal meatus was unaffected.

As compared to DEAE-dextran 5% w/v, sodium taurodihydroxy-fusidate (STDHF) administered in the same way to rats and incubated for 60 minutes (insulin 100 IU/ml with STDHF 1% w/v) resulted in obvious disruption to the nasal epithelium. Large volumes of mucus were apparent together with cell loss, epithelium rearrangement and considerable reduction of epithelium height to about half that on the undosed side. Generally, the full length of the dosed septum and turbinates were affected. AB staining showed that some mucus remained in many of the epithelial cells, but others had discharged their whole mucus content, particularly where the epithelium was reduced to a thin single cell layer, such as in the middle meatus.

Some mucus was apparent on the undosed septum or drained into the dorsal meatus, but with no cell loss. The undosed turbinates were unaffected. Epithelial height on the dosed side was consistently less than that on the undosed control side.

EXAMPLE 4

Insulin Plus Chitosan in the Rat

This Example was performed to evaluate the effect of chitosan, low or medium viscosity water soluble formulations (Sea Cure$_+$), at different concentrations and at pH values of 4 and 7.3 to 7.4 on the intranasal absorption of insulin in rats (n=4).

Semisynthetic Na-insulin and chitosan (Sea Cure$^+$) (water soluble powder) low viscosity (l.v.) and medium viscosity (m.v) from Protan Laboratories Inc. were used.

All insulin solutions were initially made in 14.65 mM phosphate buffer of pH 7.3 to 7.4 prepared from 1.904 g/l $Na_2HPO_4$ $Na_2HPO_4 \cdot 2H_2O$ and 0.616 g/l $NaH_2PO_4 \cdot 2H_2O$ in double distilled water. Adjustment of the pH to 4 where necessary was made by the addition of 150 µl of 0.1M HCl per ml of solution. Each 1 mg of insulin was considered equivalent to 28 IU. Double-strength insulin stock solutions were prepared freshly as follows: 159.9 IU/ml (6.74 mg/ml) for administration at pH 7.3 to 7.4 and 183.8 IU/ml (7.75 mg/ml) for administration at pH 4, accounting for the dilution by the addition of 0.1M HCl. The expected water content of the insulin is 15.3%.

Double strength chitosan solutions were prepared as follows: 0.2% w/v l.v. (2 mg/ml) for use at pH 7.3–7.4; 1.0% w/v l.v. (10 mg/ml) for use at pH 7.3–7.4; 0.2% w/v l.v. (2.3 mg/ml) for use at pH 4; 1.0% w/v l.v. (11.5 mg/ml) for use at pH 4; and 0.2% w/v m.v. (2.3 mg/ml) for use at pH 4.

Insulin/chitosan formulations were prepared by mixing equi-volumes of the appropriate stock insulin and chitosan solutions and the addition of 150 µl/ml of 0.1M HCl where necessary. Solutions were administered intranasally to rats at 100 µl/kg, corresponding to doses of 8 IU/kg insulin with 0.1 or 0.5 mg/kg l.v. chitosan or 0.1 mg/kg m.v. chitosan. A dose of 100 µl/kg of insulin (167 IU/ml) is instilled into the nasal cavity via a microsyringe (Hamilton) and 0.61 mm o.d. polypropylene tubing (Portex).

Blood samples of 150 µl (8–12 drops) were collected from the carotid artery in fluoride oxalate blood tubes at 10, 6 and 2 minutes pre-administration and 5, 10, 15, 20, 40, 60, 90, 120, 180 and 240 minutes post-administration. Fluid replacement was given in the form of 0.9% saline via the jugular vein. The glucose levels of the samples were assayed within 2 hours of being taken using the glucose oxidase method on a Yellow Springs 23AM glucose analyser. The pH 4 solutions were not buffered systems. A suitable buffered system also may be prepared if needed.

All of the formulations gave a rapid fall in blood glucose levels, the 0.5% l.v. pH 4.0 solution reducing the level from 100% to about 16% after 60 minutes. Generally, 0.5% material was more effective than 0.1% and pH 4.0 was better than pH 7.3 to 7.4.

EXAMPLE 5

Administration of Insulin Plus Chitosan to Sheep

Semi-synthetic human Na-insulin supplied by Nordisk, Gentofte was used. The water content of the sample was determined by spectrophotometry to be approximately 15%. Chitosan Sea Cure$^+$, which is water soluble, of low (intrinsic viscosity 388 ml/g) and medium viscosity (intrinsic viscosity 1010 ml/g) were obtained from Protan Laboratories Inc. These will be referred to as CSN LV and CSN MV, respectively. Sixteen cross-bred sheep of known weight were used. The animals were not fasted prior to insulin administration. An in-dwelling Viggo secalon cannula of 1.2 mm i.d., fitted with a secalon universal flow-switch, was placed approximately 15 cm into one of the external jugular veins of each animal on the first day of the study and, whenever necessary, was kept patent by flushing it with heparinised normal saline (25 IU/ml). This cannula was removed upon the completion of the study.

An insulin solution of 19.32 mg/ml (460 IU/ml) was prepared in 14.65 mM phosphate buffer (0.476 g $Na_2HPO_4 \cdot 2H_2O$+0.154 g $Na_2PO_4 \cdot 2H_2O$ in 250 ml water) of pH 7.3 to 7.4, and filtered on a 0.2 µm membrane filter (CORNING 21052-25). Chitosan solutions were prepared in 14.65 mM phosphate buffer as follows: 2.3 mg/ml CSN LV, 11.5 mg/ml CSN LV, 2.3 mg/ml CSN MV or 11.5 mg/ml CSN MV. Insulin/chitosan formulations were produced by mixing equal volumes of the insulin stock solution and the appropriate chitosan solution, followed by the addition of 0.15 ml of 0.166M hydrochloric acid for each 1.0 ml of the mixture. The addition of hydrochloric acid proved necessary to ensure that the chitosan remained in solution. The final formulations thus produced had the following compositions:

Formulation 1: 200 IU/ml insulin+0.1% CSN LV, pH 3.6
Formulation 2: 200 IU/ml insulin+0.5% CSN LV, pH 4.4
Formulation 3: 200 IU/ml insulin+0.1% CSN MV, pH 3.6
Formulation 4: 200 IU/ml insulin+0.5% CSN MV, pH 4.4

The sheep were divided into 4 groups, each of 3 animals, with each sheep receiving 2.0 IU/kg insulin intranasally in the form of an aqueous solution of Formulation 1, 2, 3 or 4, corresponding to Groups 1 to 4.

For the intranasal studies, the sheep were sedated by use of an i.v. dose of ketamine hydrochloride at 2.25 mg/kg. This was intended as a counter-measure against the animal sneezing during administration. The anaesthesia lasted for about 3 minutes. Blood samples of 6 ml were collected onto crushed ice from the cannulated jugular vein of the sheep at 15 and 5 min prior to the insulin administration and at various times post-administration. Each blood sample was divided into two parts. For insulin analysis, the blood collected (4.0 ml) was mixed gently in 5 ml heparinised (Li Heparin) tubes. For glucose analysis, the blood collected (2.0 ml) was mixed gently in 5 ml fluoride oxalate tubes. The plasma was separated by centrifugation at 4° C. and 3000 rpm, and then stored at −20° C. prior to insulin and glucose analysis. The following results were obtained:

TABLE 2

| | Mean blood glucose level (mmol/l) | |
| --- | --- | --- |
| | 5 mins post-administration | 75 mins post-administration |
| Group 1 | 3.4 | 3.0 |
| Group 2 | 3.4 | 2.5 |
| Group 3 | 3.4 | 2.6 |
| Group 4 | 3.8 | 1.8 |

Modifications and variations of the present invention will be obvious to those skilled in the art from the foregoing detailed description. Such modifications and variations are intended to come within the scope of the following claims.

We claim:
1. A pharmaceutical composition comprising:
a pharmacologically active agent and a polycationic polymer comprising a plurality of cationic groups, in a pharmaceutically acceptable carrier;
wherein (i) the polycationic polymer is not a polyamino acid which chelates calcium or magnesium ions, (ii) the composition does not consist of microcapsules coated with DEAE-dextran, and (iii) if for administration to gut mucosa, the composition does not consist of the active compound and a solution of DEAE-dextran.

2. The composition of claim 1 wherein the polycationic polymer is selected from the group consisting of polyaminoacids, polyquaternary compounds, protamine, polyvinylpyridine, polythiodiethylaminomethyl-ethylene, poly-p-aminostyrene, polycationic carbohydrates other than chitosan in a carrier suitable only for topical administration, polyimines, polymers derivatized with DEAE, polymethacrylates, polyacrylates, polyoxethanes, and polyamidoamines.

3. The composition of claim 1 wherein the composition is suitable for administration to mucosa of a mammal and remains at the site of administration for a sufficient time to permit systemic delivery of the pharmacologically active agent to the mammal.

4. The composition of claim 1 in the form of microspheres.

5. The composition of claim 1 in the form of a powder.

6. The composition of claim 1 in the form of a dispersion.

7. The composition of claim 1 wherein the composition is dispersed in a solution.

8. The composition of claim 7 wherein the concentration of the polycationic polymer is between about 0.01% and 50% weight/volume.

9. The composition of claim 1 comprising a complex of the polycationic polymer and the pharmacologically active agent.

10. The composition of claim 9 wherein the polycationic polymer and the pharmacologically active agent are ionically complexed.

11. The composition of claim 9 wherein the polycationic polymer and the pharmacologically active agent are covalently complexed.

12. The composition according to claim 1 wherein the pharmacologically active agent is selected from the group consisting of insulin, antimicrobial agents, anesthetics, vasoconstrictors, vasodilators, cardiotonics, enzymes, anti-inflammatories, hormones, bone metabolism controlling agents, hypotensives, sedatives, anti-tumor agents, antihistamines, antitussive, vaccines and asthma treatments.

13. The composition of claim 1 wherein the pharmacologically active agent is a nucleic acid.

14. The composition of claim 13 wherein the polycationic polymer is a chitosan compound.

15. The composition of claim 13 wherein the pharmacologically active agent is a gene.

16. The composition of claim 15 wherein the polycationic polymer is a chitosan compound.

17. The composition of claim 13 wherein pharmacologically active agent is an antisense nucleotide.

18. The composition of claim 17 wherein the polycationic polymer is a chitosan compound.

19. The composition of claim 13 wherein pharmacologically active agent is selected from the group consisting of a ribonucleic acid and a deoxyribonucleic acid.

20. The composition of claim 19 wherein the polycationic polymer is a chitosan compound.

21. The composition of claim 1 wherein the polycationic polymer is selected from the group consisting of DEAE-dextran where the dextran has a molecular weight in excess of 9000, DEAE imine, DEAE methacrylate, DEAE acrylamide, polylysine, polyhistidine, polyvinylpyrrolidonedimethylaminomethylmethacrylates and polyvinylpyrrolidonemethylacrylaminopropyl ammonium chlorides.

22. A pharmaceutically acceptable formulation comprising a complex of nucleic acid and a chitosan compound.

23. The formulation of claim 22 wherein the nucleic acid and chitosan, complex is isolated in solid form.

24. A pharmaceutical composition comprising a complex of a nucleic acid and a polycationic polymer in a pharmaceutically acceptable carrier, to permit the transport of a pharmaceutically effective amount of the nucleic acid to a patient across mucosal surfaces.

25. A method of administering a pharmacologically active agent to a mammal in a pharmaceutically effective amount, the method comprising:
administering to a mammal a composition including a pharmacologically active compound and a polycationic polymer comprising a plurality of cationic groups, in a pharmaceutically acceptable carrier;
wherein (i) the polycationic polymer is not a polyamino acid which chelates calcium or magnesium ions, (ii) wherein the composition does not consist of microcapsules coated with DEAE-dextran, (iii) if for administration to gut mucosa, the polycationic polymer does not comprise DEAE-dextran, and (iv) if in the form of a tablet for retention in the mouth, the composition does not comprise chitosan, or a salt or derivative thereof.

26. The method of claim 25 wherein the polycationic polymer is selected from the group consisting of polycationic carbohydrates, polyaminoacids, polyquaternary compounds, protamine, polyimines, polymers derivatized with DEAE, polyvinylpyridine, polymethacrylates, polyacrylates, polyoxethanes, polyamidoamines, polythiodiethylamino methylethylene, and poly-p-aminostyrene.

27. The method of claim 25 wherein the method comprises administering the composition to a mucosal surface of the mammal and allowing the composition to remain in contact with mucosa for a time sufficient for the pharmacologically active agent to pass through the mucosa for systemic distribution of a pharmaceutically effective amount of the active compound in the mammal.

28. The method of claim 27 wherein the site of administration is selected from the group consisting of nasal mucosa, vaginal mucosa and gut mucosa of said mammal.

29. The method of claim 25 wherein the composition comprises a complex of the polycationic polymer and the pharmacologically active agent.

30. The method of claim 25 wherein the pharmacologically active agent is selected from the group consisting of insulin, antimicrobial agents, anesthetics, vasoconstrictors, vasodilators, cardiotonics, enzymes, anti-inflammatories, hormones, bone metabolism controlling agents, hypotensives, sedatives, anti-tumor agents, antihistamines, antitussive, vaccines, asthma treatments, analgesics and anti-migraine agents.

31. The method of claim 25 wherein the polycationic polymer is selected from the group consisting of DEAE-dextran where the dextran has a molecular weight in excess of 9000, DEAE imine, DEAE methacrylate, DEAE acrylamide, polylysine, polyhistidine, polyvinylpyrrolidonedimethylaminomethylmethacrylates and polyvinylpyrrolidonemethylacrylaminopropyl ammonium chlorides, polyamidoamines, and cationic starches.

32. The method of claim 25 wherein the pharmacologically active agent is a nucleic acid.

33. The method of claim 32 wherein the polycationic polymer is a chitosan compound.

34. The method of claim 25 wherein the pharmacologically active agent is a gene.

35. The method of claim 34 wherein the polycationic polymer is a chitosan compound.

36. The method of claim 25 wherein pharmacologically active agent is an antisense nucleotide.

37. The method of claim 36 wherein the polycationic polymer is a chitosan compound.

38. The method of claim 25 wherein the pharmacologically active agent is selected from the group consisting of a ribonucleic acid and a deoxyribonucleic acid.

39. The method of claim 38 wherein the polycationic polymer is a chitosan compound.

40. A method for delivery of a nucleic acid in a therapeutically effective amount to a mammal, the method comprising administering to the patient a complex of the nucleic acid and a polycationic polymer.

41. The method of claim 40 wherein the polycationic polymer is a chitosan compound.

* * * * *